United States Patent [19]

David

[11] Patent Number: 5,716,547
[45] Date of Patent: Feb. 10, 1998

[54] STABLE COLLOIDAL DISPERSIONS OF RARE EARTH COMPOUNDS

[75] Inventor: Claire David, Paris, France

[73] Assignee: Rhone-Poulenc Chimie, Courbevoie Cedex, France

[21] Appl. No.: 55,772

[22] Filed: May 3, 1993

Related U.S. Application Data

[63] Continuation of Ser. No. 714,999, Jun. 14, 1991, abandoned, which is a continuation of Ser. No. 238,587, Aug. 31, 1988, abandoned.

[30] Foreign Application Priority Data

Sep. 14, 1987 [FR] France ................... 87/12669

[51] Int. Cl.⁶ ............... B01N 13/00; C01F 17/00
[52] U.S. Cl. ........... 252/313.1; 252/314; 502/304; 423/21.1; 423/263; 534/16
[58] Field of Search ............... 252/313.1, 314; 502/304; 423/21.1, 263; 534/15, 16

[56] References Cited

U.S. PATENT DOCUMENTS

| | | | |
|---|---|---|---|
| 3,024,199 | 3/1962 | Pasfield | 252/313.1 |
| 3,082,103 | 3/1963 | Wainer | 252/313.1 X |
| 3,148,151 | 9/1964 | Fitch et al. | 252/313.1 |
| 3,476,691 | 11/1969 | Smith et al. | 252/313.1 |
| 4,181,532 | 1/1980 | Woodhead | 252/313.1 X |
| 4,231,893 | 11/1980 | Woodhead | 252/313.1 |
| 4,356,106 | 10/1982 | Woodhead et al. | 252/313.1 |
| 4,647,401 | 3/1987 | Gradeff et al. | 534/15 X |
| 4,770,671 | 9/1988 | Monroe et al. | 51/293 |
| 4,801,399 | 1/1989 | Clark et al. | 252/315.01 |
| 5,132,048 | 7/1992 | Picard-Seon et al. | 252/313.1 |

OTHER PUBLICATIONS

Hawley, G.G. *The Condensed Chemical Dictionary*, 11th Ed. Van Nostrand Rheinhold, Co. NY, 1981 Month unavailable. p. 1079.

Hawley, G.G., *The Condensed Chemical Dictionary*, 10th Ed. (Van Nostrand Reinhold Co, NY, 1981 Month unavailable.) p. 1104.

*The Merck Index of Chemicals and Drugs*, 7th ed. (Merck & Co., Inc., Rahway, NJ, 1960 Month unavailable.) p. 1112.

Chemical Abstracts, vol. 108, Apr. 25, 1988 No. 149920f.

*Primary Examiner*—Richard D. Lovering
*Assistant Examiner*—Daniel S. Metzmaier
*Attorney, Agent, or Firm*—Burns, Doane, Swecker & Mathis, L.L.P.

[57] ABSTRACT

Stable colloidal dispersions, in water, of rare earth compounds, e.g., yttric rare earth compounds, are produced by (a) reacting, in an aqueous reaction medium, a rare earth oxide with a controlled effective amount of a monovalent water-soluble acid having a $pK_a$ of from 2.5 to 5.0, and then (b) heating the resulting medium of reaction.

26 Claims, No Drawings

5,716,547

STABLE COLLOIDAL DISPERSIONS OF RARE EARTH COMPOUNDS

This application is a continuation of application Ser. No. 07/714,999, filed Jun. 14, 1991, now abandoned, which application is a continuation of application Ser. No. 07/238,587, filed Aug. 31, 1988, now abandoned.

BACKGROUND OF THE INVENTION

1. Field of the Invention

The present invention relates to novel colloidal dispersions of rare earth compounds in an aqueous medium and to a process for the production thereof. This invention especially relates to colloidal dispersions of a yttric rare earth compound.

As utilized herein, the term "yttric rare earth" is intended to connote the heaviest elements of the rare earths, corresponding to atomic numbers beginning with samarium and terminating with lutetium, and including yttrium.

2. Description of the Prior Art

In U.S. Pat. No. 3,024,199 a process is described for the preparation of aqueous sols of hydrated oxides of the rare earths, said process comprising:

(i) contacting an aqueous solution of a monovalent rare earth salt with ammonia in order to precipitate the corresponding hydrated rare earth oxide;

(ii) eliminating the major fraction of the ammonium salts, while maintaining, by controlling the free ammonia content, the pH in the range of from 9.5 to 10.5; and (iii) separating the hydrated rare earth oxide, then peptizing it by heating to a temperature in the range of 60° to 100° C.

The resulting sols of hydrated rare earths have a concentration, expressed in terms of rare earth oxide content, of from 10 to 50% by weight, with the particle sizes varying from 5 to 200 millimicrons, with a length/diameter ratio of about 1:1 to 5:1, have a pH of 7.0 to 8.3, and contain a stabilizing monovalent anion, with the molar ratio of rare earth oxide/monovalent stabilizing anion ranging from 6.6:1 to 165:1.

The sols of hydrated rare earths thus have a formula close to that of the true hydroxides of the rare earths.

SUMMARY OF THE INVENTION

A major object of the present invention is the provision of an improved, simpler process for the production of novel colloidal dispersions of rare earth compounds in an aqueous medium hereinafter designated a "sol", and which improved process requires neither the numerous stages, nor the difficulty handled and freshly prepared hydrated rare earth oxide, nor the large amounts of ammonia that characterize the current state of this art.

Briefly, the present invention features reacting a rare earth oxide with a controlled amount of a water-soluble monovalent acid having a $pK_a$ of from 2.5 to 5.0, and then heating the resulting reaction medium.

DETAILED DESCRIPTION OF THE PREFERRED EMBODIMENTS OF THE INVENTION

More particularly according to the present invention, the subject process enables the direct production of a sol having the distinguishing characteristics reported below.

A rare earth oxide in the sesquioxide form is used advantageously in the process of the invention.

Preferably, an oxide of a yttric rare earth is employed, and even more preferably a yttrium oxide, $Y_2O_3$, or a holmium oxide, $Ho_2O_3$.

It is desirable that the oxide used be of high purity, preferably greater than or equal to 99% and, more preferably, an oxide having a purity of 99.99% is used.

The rare earth oxide is present in the form of a fine powder, the particle size of which is on the order of a few microns and the mean diameter of which characteristically ranges from 1 to 5 μm. The mean diameter is defined as a diameter such that 50% by weight of the particles have a diameter smaller or larger than the mean diameter.

In a preferred embodiment of the invention, a rare earth oxide is used which has been subjected to calcination at a temperature of 850° to 1050° C., preferably about 950° C. The duration of the calcination preferably ranges from 2 to 4 hr.

As regards the acid, its selection is governed by the requirements that it must be soluble in water, be monovalent and have a $pK_a$ of from 2.5 to 5.0.

Acetic acid is well suited for use in the process of the invention.

Preferably an acid devoid of impurities is used. Its initial concentration is not critical and it may be diluted, for example to 1N, or concentrated to 17N. Generally, the solution of said acid ranges from 1 to 4N, as it constitutes the dispersion medium of the rare earth oxide and thus must constitute a sufficiently large liquid phase to carry out the attack under good conditions of agitation.

The amount of the acid used is an important element in the process according to the invention. It must be present in a stoichiometric deficit, which signifies that the molar ratio of the acid used to the rare earth oxide, expressed as the metallic cation thereof, is less than 2.5 and greater than 1.

The lower limit is defined on the basis of the economic requirements of good reaction yields and favorable reaction kinetics.

Preferably, such molar ratio ranges from 1.1 to 2.2 and more preferably from 1.2 to 1.8.

According to a practical embodiment of the invention, the rare earth oxide is added to the acid solution, the concentration of which is adjusted such that it corresponds to the aforementioned limits.

In another embodiment of the invention, the rare earth oxide is suspended in water and the acid is subsequently added in sufficient amounts.

This operation is carried out in both cases under agitation and at ambient temperature, most typically ranging from 15° to 25° C.

The second stage of the process of the invention entails subjecting the reaction medium to a heat treatment at a temperature from 50° C. to the reflux temperature of the reaction medium. Such treatment is preferably carried out at a temperature of from 70° to 100° C.

The duration of this treatment is highly variable and becomes shorter with increasing temperatures.

Once the reaction temperature is attained, it is maintained for 1 to 4 hr and preferably for 3 to 4 hr.

The formation of a sol of a rare earth compound is observed and the potential presence of a residue consisting essentially of unreacted rare earth oxide is noted, if the rare earth oxide has been treated at a temperature less than 70° C.

A preferred embodiment of the invention includes separating said residue by solid/liquid separation technique: filtration, decantation or centrifugation.

The separation is preferably carried out by centrifugation, and a colloidal dispersion of a rare earth compound in an aqueous medium is thus produced.

According to the present invention, the rare earth compound is present in the form of a colloidal dispersion in water, which signifies that said compound has particles of colloidal dimensions, but does not exclude the presence of a rare earth in the ionic state.

The proportion of the rare earth in the colloidal form preferably ranges from 85% to 100%.

Said dispersion may have a concentration in the rare earth compound, expressed as the rare earth oxide thereof, of up to 1 mole/liter.

Its pH is close to neutrality and more precisely ranges from 6.0 to 7.5.

The chemical composition of the colloids is determined on the residue obtained after the ultracentrifugation of the dispersion, by analyzing the rare earth by the complexometric method via EDTA and by acidimetric analysis in return of the monovalent anion emanating from the acid.

It corresponds to the following chemical formula (I):

$$RE\ (A)_x(OH)_{3-x} \tag{I}$$

in which:

RE represents the rare earth cation, preferably a yttric cation;

A represents the anion of the monovalent water-soluble acid, having a $pK_a$ of from 2.5 to 5; and x is a number less than 2.5 and greater than 1, preferably ranging from 1.1 to 2.2 and even more preferably from 1.2 to 1.8.

The preferred sols of the invention are those of a rare earth compound corresponding to formula (I) in which RE represents yttrium or holmium, and A the acetate anion with x ranging from 1.1 to 2.2 and, preferably from 1.2 to 1.8.

The colloids obtained according to the invention are spherical in shape.

The size of the colloids is defined by the measure of the hydrodynamic diameter of the colloids, determined by the quasi-elastic diffusion of light, according to the method described by Michael L. McConnell in *Analytical Chemistry*, Vol. 53, No. 8, 1007 A (1981). It ranges from 10 to 2,000 Å and the mean hydrodynamic diameter of the colloids ranges from 30 to 100 Å.

It should be noted that the sols obtained by the process of the invention are perfectly stable under the usual storage conditions. Such storage is preferably at a temperature lower than ambient and more preferably ranges from 5° to 10° C.

In order to further illustrate the present invention and the advantages thereof, the following specific examples are given, it being understood that same are intended only as illustrative and in nowise limitative. In said examples to follow, the properties of the resultant sols are reported.

EXAMPLE 1

Into a 2 liter reactor equipped with a thermometer, agitating means, a system for the introduction of the reagents, a reflux condenser, a heating device and a unit to measure the pH, 1,000 cm³ of a 2N acetic acid solution were introduced.

In said medium, 173 g yttrium oxide of 99.99% purity (marketed by Rhone-Poulenc under the quality designation of luminophore) were dispersed by mechanical agitation.

Subsequently, heating was commenced and when the temperature of 70° C. was reached, it was maintained for 3 hr, 30 min.

The formation of a sol of a yttrium compound was observed and the presence of a residue consisting essentially of unreacted yttrium oxide was noted, which could be separated as described hereinafter and optionally recycled into the attack stage.

The reaction medium was subjected to a centrifugation operation by means of a JOUAN centrifuge, 3,500 rpm for 20 min.

The supernatant was removed.

The coarse particles entrained were eliminated by filtration on millipore paper, the pore diameter of which was larger than 1 μm.

A yield of the attack reaction of 99% was determined.

A sol of the yttrium compound corresponding to the following chemical formula was obtained: $Y(OH)_{1.7}(CH_3COO)_{1.3}$; it had a concentration, expressed as $Y_2O_3$, equal to 182 g/l and a pH equal to 6.8.

The percentage of yttrium in the colloidal form was determined by analyzing the total yttrium in the supernatant solution obtained after ultracentrifugation (45,000 rpm—1 h) by complexometric titration with a titered EDTA solution. The analysis of yttrium in the supernatant solution made it possible to determine a percentage of yttrium in the colloidal form of 95%.

The size of the colloids was characterized by the quasi-elastic diffusion of light according to the method described by Michael L. McConnell in *Analytical Chemistry*, Vol. 53, No. 8, 1007 Å (1981). The mean hydrodynamic diameter of the colloids was on the order of 41 Å.

It was noted that the resulting sol had a stability of at least one month in storage at 5° C.

EXAMPLE 2

Into a reactor such as described in Example 1, 1,000 cm³ of a 2N acetic acid solution were introduced.

In said medium, 173 g yttrium oxide of a purity of 99.99% were dispersed by mechanical agitation, said oxide being marketed by Rhone-Poulenc under the quality designation of luminophore.

Subsequently, the dispersion was heated and when the temperature of 100° C. was reached, it was maintained for 1 hr.

The formation of a sol of a yttrium compound was observed.

A yield of 99% of the attack reaction was determined.

A sol of a yttrium compound corresponding to the following chemical formula was obtained: $Y(OH)_{1.7}(CH_3COO)_{1.3}$, having a concentration, expressed in $Y_2O_3$, equal to 182 g/l and a pH of 6.7.

The percentage of yttrium in the colloidal form was 95%.

The mean hydrodynamic diameter of the colloids was 43 Å.

The resulting sol obtained had a stability of at least one month in storage at 5° C.

EXAMPLE 3

Into a reactor such as described in Example 1, 1,000 cm³ of a 2N acetic acid solution were introduced.

In said medium, 290 g holmium oxide of a purity of 99.99%, also marketed by Rhone-Poulenc, were dispersed by mechanical agitation.

Heating was then commenced and when a temperature of 70° C. was reached, it was maintained for 3 hr, 30 min.

The formation of sol of a holmium compound was observed and the presence of a residue consisting essentially of unreacted holmium oxide was noted; it could be separated as described below and optionally recycled into the attack stage.

The reaction medium was subjected to centrifugation in a JOUAN centrifuge, at 3,500 rpm, for 20 min.

The supernatant was removed.

The coarse particles entrained were eliminated by filtration on millipore paper, the pore diameter of which was larger than 1 μm.

A sol of a holmium compound corresponding to the following chemical formula was produced: $Ho(OH)_{1.7}(CH_3COO)_{1.3}$, having a concentration, expressed in $Ho_2O_3$, equal to 290 g/l and a pH equal to 7.1.

The percentage of holmium in the colloidal form was 82%.

The mean hydrodynamic diameter of the colloids was 45 Å.

The resulting sol had a stability in storage at 5° C. of at least one month.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a colloidal dispersion of an yttric rare earth compound in water, comprising (a) reacting, in an aqueous reaction medium, an yttric oxide with a controlled amount, effective to prepare said dispersion upon heating, of a monovalent water-soluble acid having a pKa of from 2.5 to 5.0, and thence (b) heating the resulting medium of reaction, said process being carried out without ammonia or ammonium compounds.

2. The process as defined by claim 1, said yttric oxide having a purity of from 99 to 99.99%.

3. The process as defined by claim 1, said yttric oxide having been calcined at a temperature of from 850° to 1050° C.

4. The process as defined by claim 3, said temperature of calcination being about 950° C.

5. The process as defined by claim 3, said yttric oxide having been calcined for from 2 to 4 hr.

6. The process as defined by claim 1, said monovalent water-soluble acid comprising acetic acid.

7. The process as defined by claim 1, the medium of reaction having an acid concentration of from 1 to 4N.

8. The process as defined by claim 1, wherein the amount of the monovalent water-soluble acid is such that the molar ratio of said acid to the ytric oxide, expressed as the metallic cation thereof, is between 1 and 2.5.

9. The process as defined by claim 8, said molar ratio ranging from 1.1 to 2.2.

10. The process as defined by claim 9, said molar ratio ranging from 1.2 to 1.8.

11. The process as defined by claim 1, comprising adding the ytric oxide to an aqueous solution of the monovalent water-soluble acid, in the concentration desired.

12. The process as defined by claim 1, comprising suspending the ytric oxide in water and adding the monovalent water-soluble acid thereto.

13. The process as defined by claim 1, comprising heating the medium of reaction to a temperature of from 50° C. to the reflux temperature thereof.

14. The process as defined by claim 13, said temperature ranging from 70° to 100° C.

15. The process as defined by claim 13, comprising maintaining said temperature for from 1 to 4 hr.

16. The process as defined by claim 15, comprising maintaining said temperature for from 3 to 4 hr.

17. The process as defined by claim 1, comprising separating a residue of reaction from said aqueous reaction medium.

18. A novel colloidal dispersion of a trivalent rare earth compound in an aqueous medium, said rare earth compound having the formula (I):

$$RE(A)_x(OH)_{3-x} \qquad (I)$$

wherein RE is an yttric rare earth cation, A is the anion of a monovalent water-soluble acid having a $pK_a$ of from 2.5 to 5 and x is a number between 1 and 2.5.

19. The colloidal dispersion as defined by claim 18, wherein A is the acetate anion.

20. The colloidal dispersion as defined by claim 18, wherein x ranges from 1.1 to 2.2.

21. The colloidal dispersion as defined by claim 20, wherein x ranges from 1.2 to 1.8.

22. The colloidal dispersion as defined by claim 18, wherein the colloids thereof are spherical in shape.

23. The colloidal dispersion as defined by claim 18, wherein the mean hydrodynamic diameter of the colloids thereof ranges from 30 to 100 Å.

24. The colloidal dispersion as defined by claim 18, having a proportion of rare earth values in colloidal form ranging from 85 to 100%.

25. The colloidal dispersion as defined by claim 18, having a concentration of said rare earth compound, expressed as the rare earth oxide thereof, of up to 1 mole/liter.

26. The colloidal dispersion as defined by claim 18, having a pH of from 6.0 to 7.5.

* * * * *